US009675749B2

(12) United States Patent
Nemoto

(10) Patent No.: US 9,675,749 B2
(45) Date of Patent: Jun. 13, 2017

(54) MEDICAL FLUID INJECTOR DEVICE

(75) Inventor: Shigeru Nemoto, Tokyo (JP)

(73) Assignee: Nemoto Kyorindo Co., Ltd., Tokyo (JP)

( * ) Notice: Subject to any disclaimer, the term of this patent is extended or adjusted under 35 U.S.C. 154(b) by 0 days.

(21) Appl. No.: 13/639,657

(22) PCT Filed: Apr. 4, 2011

(86) PCT No.: PCT/JP2011/058557
§ 371 (c)(1),
(2), (4) Date: Oct. 5, 2012

(87) PCT Pub. No.: WO2011/125987
PCT Pub. Date: Oct. 13, 2011

(65) Prior Publication Data
US 2013/0030290 A1   Jan. 31, 2013

(30) Foreign Application Priority Data

Apr. 6, 2010   (JP) .................................. 2010-087882

(51) Int. Cl.
*A61M 5/00* (2006.01)
*A61M 5/145* (2006.01)
*A61M 5/168* (2006.01)

(52) U.S. Cl.
CPC ........ *A61M 5/007* (2013.01); *A61M 5/14546* (2013.01); *A61M 5/14566* (2013.01); *A61M 5/16827* (2013.01); *A61M 2205/505* (2013.01)

(58) Field of Classification Search
CPC ........ A61M 3/00; A61M 11/00; A61M 15/00; A61M 25/00; A61M 5/14546;
(Continued)

(56) References Cited

U.S. PATENT DOCUMENTS 5,840,026 A    11/1998  Uber, III et al.
5,915,379 A *  6/1999   Wallace et al. .......... 128/204.21
(Continued)

FOREIGN PATENT DOCUMENTS

CN   1665562 A   9/2005
CN   1822869 A   8/2006
(Continued)

OTHER PUBLICATIONS

International Preliminary Report on Patentability issued in PCT/JP2011/058557, mailed Nov. 22, 2012.
(Continued)

*Primary Examiner* — Bhisma Mehta
*Assistant Examiner* — Hamza Darb
(74) *Attorney, Agent, or Firm* — Knobbe, Martens, Olson & Bear, LLP

(57) ABSTRACT

A medical fluid injector device injecting a patient with a mixed medical fluid and capable of simply setting injection conditions for the mixed medical fluid. A medical fluid injector includes an injector head injecting a diluted contrast medium into a patient and a controller unit. The controller unit receives an input relating to an injection rate of the diluted medical fluid receives an input relating to a mixture ratio by an operator, calculates an injection rate of a contrast medium based on the mixture ratio, and calculates an injection rate of physiological saline based on the mixture ratio. The injector head injects the contrast medium and the physiological saline at the calculated injection rate of the contrast medium and the calculated injection rate of the physiological saline, respectively.

6 Claims, 6 Drawing Sheets

(58) Field of Classification Search
CPC ......... A61M 5/14566; A61M 5/16827; A61M 2205/505; A61J 7/00
USPC ........ 700/28; 604/890, 246, 4.01, 890.1, 30, 604/31, 65, 66, 131; 600/431
See application file for complete search history.

(56) References Cited

U.S. PATENT DOCUMENTS

| | | | |
|---|---|---|---|
| 7,292,227 B2* | 11/2007 | Fukumoto et al. | 345/173 |
| 7,753,049 B2* | 7/2010 | Jorczak et al. | 128/205.24 |
| 2004/0064041 A1* | 4/2004 | Lazzaro et al. | 600/432 |
| 2005/0273059 A1 | 12/2005 | Mernoe et al. | |
| 2005/0277833 A1* | 12/2005 | Williams | A61M 5/16827 600/431 |
| 2006/0079768 A1* | 4/2006 | Small et al. | 600/432 |
| 2006/0184122 A1 | 8/2006 | Nemoto | |
| 2007/0213662 A1 | 9/2007 | Kalafut et al. | |
| 2007/0282263 A1 | 12/2007 | Kalafut et al. | |
| 2008/0177126 A1* | 7/2008 | Tate et al. | 600/5 |

FOREIGN PATENT DOCUMENTS

| | | |
|---|---|---|
| EP | 1449550 | 8/2004 |
| JP | A-2001-149360 | 6/2001 |
| JP | A-2006-511263 | 4/2006 |
| JP | 2008-500119 A | 1/2008 |
| JP | A-2008-521506 | 6/2008 |
| JP | A-2009-89817 | 4/2009 |
| JP | B-4417621 | 2/2010 |
| WO | WO 03/101527 A1 | 12/2003 |
| WO | WO 2005/118031 | 12/2005 |
| WO | WO 2007/116840 A1 | 10/2007 |

OTHER PUBLICATIONS

Office Action issued Mar. 4, 2014 in Chinese Patent Application No. 201180027928.3.
Office Action in Chinese Patent Application No. 201180027928.3, mailed on Dec. 31, 2014.
Office Action in corresponding Japanese Patent Application No. 2012-509657, dated Dec. 22, 2015.
Extended European Search Report in European Patent Application No. 11765887.2, dated Oct. 11, 2016.

* cited by examiner

MEDICAL FLUID INJECTOR DEVICE

RELATED APPLICATIONS

This application is the U.S. National Phase under 35 U.S.C. §371 of International Application No. PCT/JP2011/058557, filed Apr. 4, 2011, designating the U.S., and published in Japanese as WO2011/125987 on Oct. 13, 2011, which claims priority to Japanese Patent Application No. 2010-087882, filed Apr. 6, 2010, the entire content of which is incorporated herein by reference.

TECHNICAL FIELD

The present invention relates to devices which injects a patient with medical fluid at various concentrations provided by mixing a plurality of medical fluids, and more particularly, to a medical fluid injector device capable of facilitating programming injection conditions for the mixed medical fluid.

BACKGROUND ART

Currently known medical imaging diagnostic apparatuses include CT (Computed Tomography) scanners, MRI (Magnetic Resonance Imaging) apparatuses, PET (Positron Emission Tomography) apparatuses, DSA (Digital Subtraction Angiography) apparatuses and the like. In using such apparatus, a medical fluid such as a contrast medium and physiological saline (hereinafter also referred to simply as a medical fluid) is often injected into the patient.

Various medical fluid injector devices for automatic injection have been conventionally proposed. For example, Patent Document 1 (WO 2007/116840) has disclosed apparatus in which a contrast medium and a physiological saline are injected simultaneously to perform injection of the contrast medium diluted at a predetermined concentration (hereinafter referred to as a "diluted contrast medium") into a patient.

For performing such injections, it is necessary to program the injection rate and the volume for both medical fluids in advance. By way of example, for injecting 20 ml of diluted contrast medium at 3.0 ml/sec, injection rate of the contrast medium is set to 1.8 ml/sec, the volume thereof is set to 12 ml, whereas the injection rate of the physiological saline is set to 1.2 ml/sec, and the volume thereof is set to 8 ml. Then, the injection of 20 ml diluted contrast medium at 3.0 ml/sec will be executed by simultaneously injecting both of the contrast medium and the saline under the injection condition.

Patent Document 1: WO2007/116840

DISCLOSURE OF INVENTION

The conventional configuration, however, requires the input relating to an injection rate and an injection volume for the contrast medium and the input relating to an injection rate and volume of the physiological saline to set the injection conditions for the diluted contrast medium. This involves considerable time and effort. Furthermore, in the conventional configuration, it is necessary to adjust the injection rate and the like for each medical fluid precisely to provide a desired dilution rate (i.e. mixture ratio.) For these reasons, there is a need to develop an easy-to-use medical fluid injector device capable of setting the injection conditions more simply.

The present invention has been made in view of the abovementioned problems, and it is an object thereof to provide a medical fluid injector device injecting a mixed medical fluid provided by mixing medical fluids into a patient and capable of facilitating programming injection conditions for the mixed medical fluid.

SUMMARY OF INVENTION

To solve the abovementioned problems, the present invention provides a medical fluid injector device including:

an injector head injecting a patient with a mixed medical fluid provided by mixing a first medical fluid and a second medical fluid;

a controller unit having a monitor, screens for programming an injection condition for the mixed medical fluid displayed on the monitor, wherein the controller unit performs:

a process of receiving an input relating to an injection rate of the mixed medical fluid;

a process of receiving an input relating to a mixture ratio or a mixture factor (hereinafter referred to as a mixture ratio or the like) between the first medical fluid and the second medical fluid performed by an operator;

a process of calculating the injection rate of the first medical fluid based on said input mixture ratio or the like;

a process of calculating the injection rate of the second medical fluid based on said input mixture ratio or the like, and the injector head injects the first medical fluid at the calculated injection rate of the first medical fluid and the second medical fluid at the calculated injection rate of the second medical fluid.

The "controller unit" may be provided as an independent apparatus or may be provided as part of the function of another device.

In the "process of receiving input of an injection rate of the mixed medical fluid," the operator may manually input the injection rate, or information about the injection rate may be read from an information storage medium such as an IC tag and may be input automatically.

According to the present invention, programming injection conditions can be completed by inputting the injection rate and the mixture ratio or the like of the mixed medical fluid.

In the medical fluid injector device according to another aspect of the present invention, the monitor is of a touch panel type, and in the process of receiving an input relating to a mixture ratio or the like, an image button for changing the mixture ratio or the like is displayed on the monitor, and the mixture ratio or the like is changed by the operator moving his fingertip or an input pen while he touches the image button with his fingertip or the input pen.

With the configuration in which the input is performed with the touch panel, more intuitive and simpler input can be achieved.

In the medical fluid injector device according to another aspect of the present invention, the controller unit further performs:

a process of receiving a change, made by the operator, relating to the mixture ratio or the like during injection of the mixed medical fluid;

a process of calculating an injection rate of the first medical fluid based on the new mixture ratio or the like; and a process of calculating an injection rate of the second medical fluid based on the new mixture ratio or the like, and the injector head injects the first medical fluid and the second medical fluid at the calculated new injection rate of the first medical fluid and the calculated new injection rate of the second medical fluid, respectively.

With the configuration, the mixture ratio or the like can be changed during the injection operation, so that the medical fluid can be injected under appropriate conditions (concentrations) for each region of interest (ROI) within a patient's body in an angiographic examination, for example.

As described above, the present invention can provide the medical fluid injector device injecting the patient with the mixed medical fluid provided by mixing medical fluids and capable of facilitating programming injection conditions for the mixed medical fluid.

BEST MODE FOR CARRYING OUT INVENTION

Figure 1:
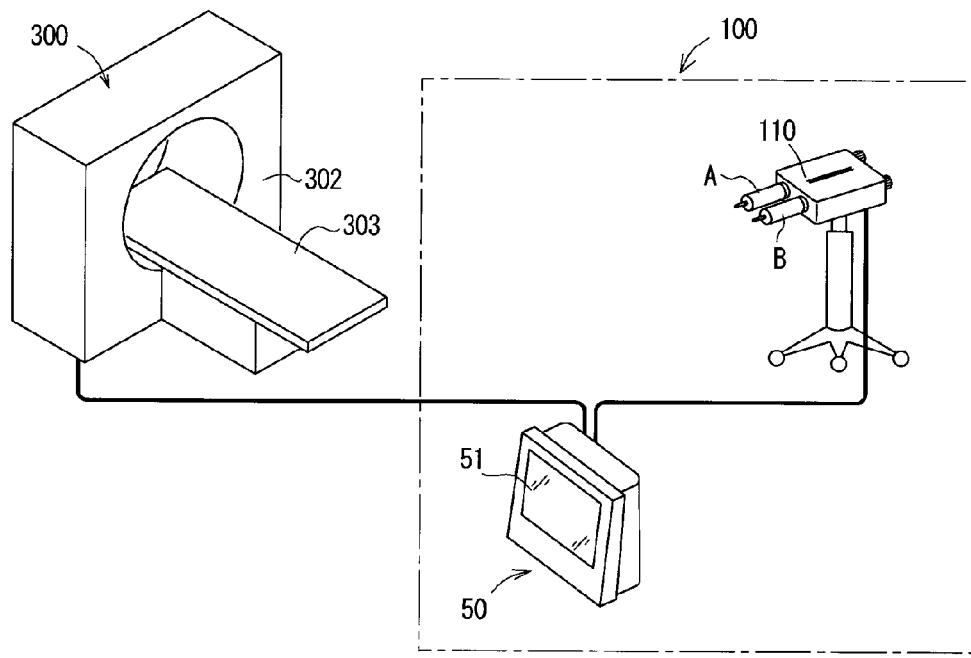
FIG. 1 is a schematic diagram of a medical fluid injector device and a system including the same according to an embodiment of the present invention.

An embodiment of the present invention will hereinafter be described with reference to the drawings. As shown in FIG. 1, an imaging diagnostic system according to the present embodiment includes a medical fluid injector device 100 and an imaging diagnostic apparatus 300 interconnected thereto. The injector device 100 includes an injector head 110 for injecting a contrast medium into a patient and a controller unit 50 for programming conditions for the injection.

A known injector head can be used as the injector head 110. In this example, a dual-type injector head may be used on which a syringe A (first syringe) filled with the contrast medium and a syringe B (second syringe) filled with physiological saline are configured to be mounted.

By way of example, the injector head 110 is supported rotatably on a caster stand. Although not shown in detail, the injector head 110 has piston driving mechanisms for pushing a piston member of each syringe. The piston driving mechanism is provided for each of syringes A and B. The piston driving mechanism has a motor serving as a driving source, a link mechanism for transferring force from the motor, and a member moving forward or rearward in response to the force transferred by the link mechanism.

The injector head 110 may also have a tag reader for reading information stored on an IC tag attached to the syringe or a protective cover (not shown) thereof. The IC tag can store information about the syringe and information about the medical fluid in the syringe when the syringe is a pre-filled type. The information about the syringe may include, for example, identification data of a syringe (for example, a lot number), data of pressure limit of a cylinder member, data of an inner diameter of the cylinder member, and data of the stroke of the piston member. The information about medical fluid may include, for example, name of medical fluid (product name), content data including an iodine amount, viscosity, and expiration date.

As shown in FIG. 1, the controller unit 50 has a monitor 51 of a touch panel type. For example, images used for setting injection conditions are displayed on the monitor 51 (described later in detail). Information about medical fluid in the syringe, information about injection pressure of the medical fluid during medical fluid injection (force to push the piston member) and the like may also be displayed on the monitor 51.

The controller unit 50 contains a computer component (not shown) which may perform: a process of receiving input of various information through the touch panel, a process of performing various calculations based on the input information, a process of controlling operations of the injector head 110, and the like. The computer component may be a so-called one-chip microcomputer and may have hardware such as a CPU (Central Processing Unit), a ROM (Read Only Memory), a RAM (Random Access Memory), and an I/F (interface). In the computer component, some programs are stored on an information storage medium such as the ROM and the CPU performs various types of processing based on the program.

The injector head 110 may be provided with a sub-monitor (not shown) of a touch panel type. A hand controller (not shown) may be connected to the controller unit 50, such that an operator can manipulate it for example to input some information.

The imaging diagnostic apparatus 300 includes a bed 303 movable horizontally with a patient lying thereon, an apparatus body 302 for taking diagnostic images of a patient, and a control unit (not shown) having a monitor, a keyboard and the like, by way of example.

Figure 2:
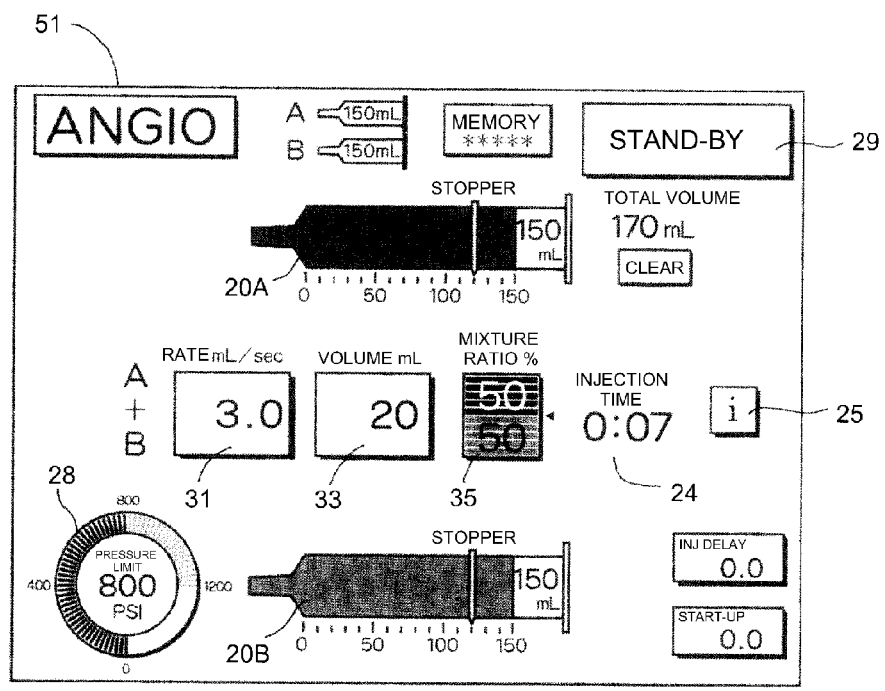
FIG. 2 is a diagram showing an image displayed on a monitor of a controller unit.

FIG. 2 shows a screen for setting injection conditions displayed on the monitor 51. On the screen, an image 20A representing the first syringe (contrast medium) is displayed in an upper portion of a central area on the screen. An image 20B representing the second syringe (physiological saline) is displayed in a lower portion of the central area on the screen.

Three images 31, 33, and 35 are displayed side by side horizontally between two syringe images 20A and 20B. The injection rate of a diluted contrast medium is displayed in the image 31, in this example, "3.0" (ml/sec) is displayed in a window. This means that the diluted contrast medium will be injected into a patient at a rate of 3.0 ml/sec. The image 31 functions as a button. As described later, when the image 31 is pressed, a numeric keypad 41 will appear (see FIG. 4). Numeric values can be input through the numeric keypad 41.

The volume of the diluted contrast medium is displayed in the image 33, in this example, "20" (ml) is displayed in a window. This means that 20 ml of the diluted contrast medium will be injected into the patient. Similarly to the image 31, the image 33 also functions as a button. When the image 33 is pressed, a numeric keypad similar to the abovementioned one will appear.

A mixture ratio of the contrast medium and the physiological saline is displayed in the image 35, in this example, "50/50" is displayed. This means that the mixture ratio of the contrast medium and the physiological saline is 50:50 (1:1). The image 35 also functions as a button. Specifically, an operator can move his fingertip up or down (by way of example) while touching a portion of image 35, to thereby change the mixture ratio (described later in detail).

As shown in FIG. 2, the following images are displayed on the screen in addition to the abovementioned ones. A section 24 for displaying an injection time shows a scheduled injection time, in this example, "0:07" (sec) is displayed. This means that medical fluid injection will be performed for 7 seconds.

Figure 3:
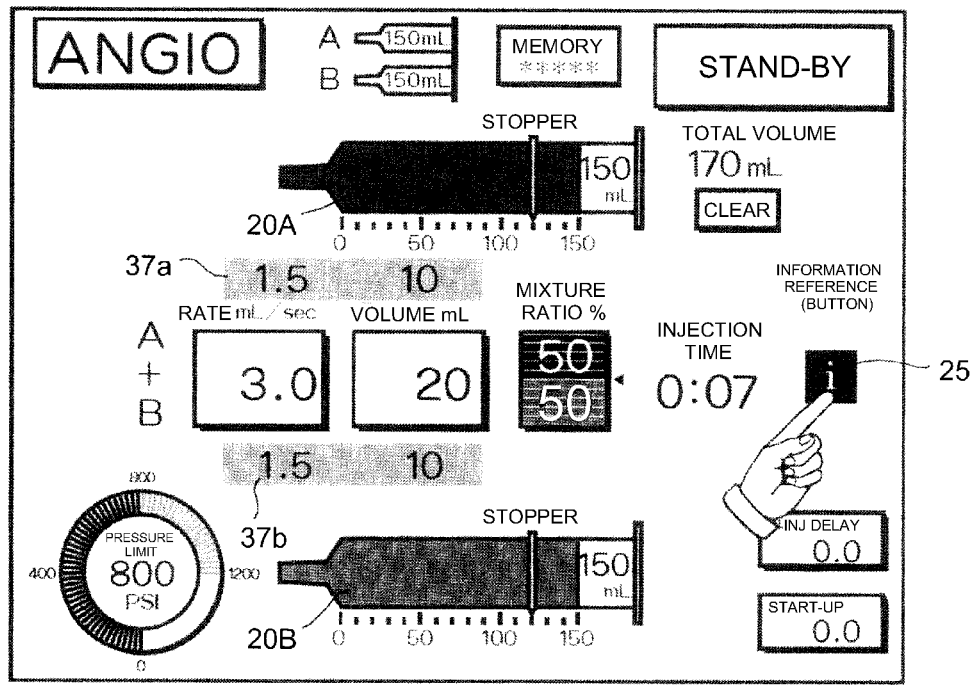
FIG. 3 is a diagram showing images displayed when an information button is pressed on the screen of FIG. 2.

An information button 25 is displayed at the right on the screen. As shown in FIG. 3, when the button 25 is pressed, an image 37*a* showing the injection rate and the volume of the contrast medium, and an image 37*b* showing the injection rate and the volume of the physiological saline are displayed. In this example, the injection rate of the contrast medium is 1.5 ml/sec and the volume thereof is 10 ml. The injection rate of the physiological saline is 1.5 ml/sec and the volume thereof is 10 ml.

In the present embodiment, these information items (the injection rate and the volume of each medical fluid) will not be displayed unless the information button 25 is pressed, by way of example. According to this configuration, the screen can be simplified such that only items relating to important information are displayed on the screen (see FIG. 2). This allows the operator to check the information on the screen easily.

Returning to the description of the images, as shown in FIG. 2, a circular indicator image 28 showing a pressure limit value is displayed at the lower left on the screen. In this example, "800" PSI is shown as the pressure limit value. A button 29 displaying "stand-by" is displayed at the upper right on the screen.

Operation of the medical fluid injector device 100 of the present embodiment configured as above will be described below specifically. It should be noted that steps described below are merely illustrative and that the present invention is not limited to the order of the steps and the like.

First, the injection rate (3.0 mL/sec in this example) of the diluted contrast medium is input (see FIG. 2). By way of example, this input may be performed by the operator selecting the image 31 to show numeric keypad 41 and inputting the numeric value through the numeric keypad 41. Alternatively, the injector head 110 may read the information stored on the IC tag attached to the syringe or the protective cover (not shown) thereof, and the information may be transmitted and automatically input to the controller unit 50.

Instead of the IC tag, magnet(s) and/or metal piece(s) that can represent predetermined information may be provided for the syringe or the protective cover.

Figure 4:
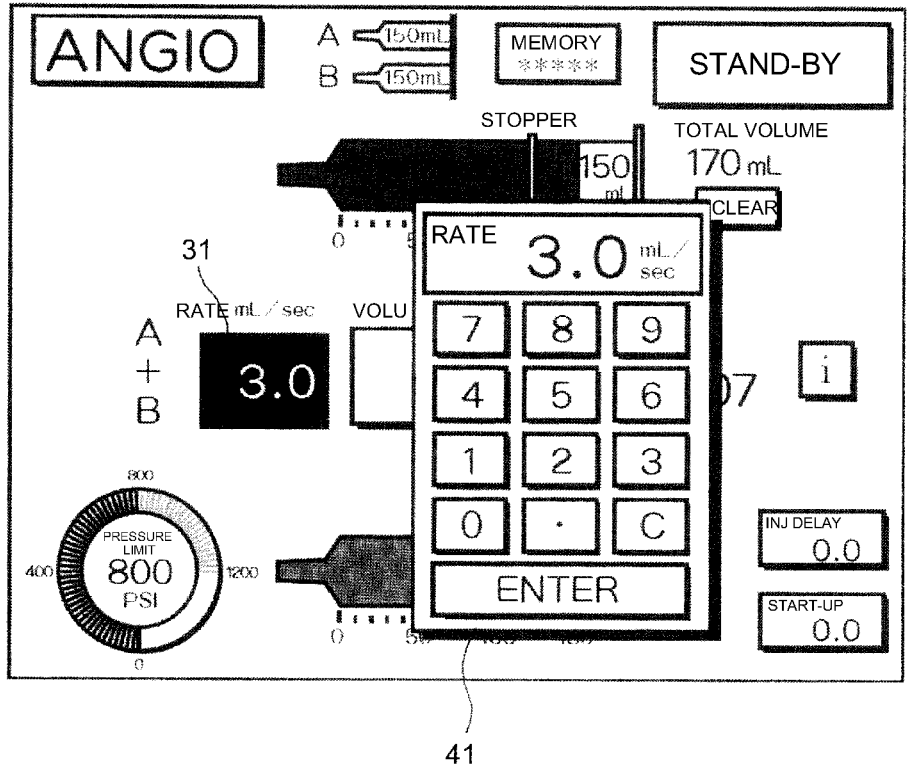
FIG. 4 is a diagram showing images displayed when an image button for an injection rate is pressed on the screen of FIG. 2.

Simultaneously with or subsequently to (by way of example) the input of the injection rate, the volume of the diluted contrast medium (20 ml in this example) may be input. The input may be performed by the operator inputting the numeric value through the numeric keypad 41 as shown in FIG. 4, similarly to the abovementioned input. Alternatively, the injector head 110 may read the information stored on the IC tag attached to the syringe or the protective cover, and the information may be transmitted and automatically input to the controller unit 50.

Figure 5:
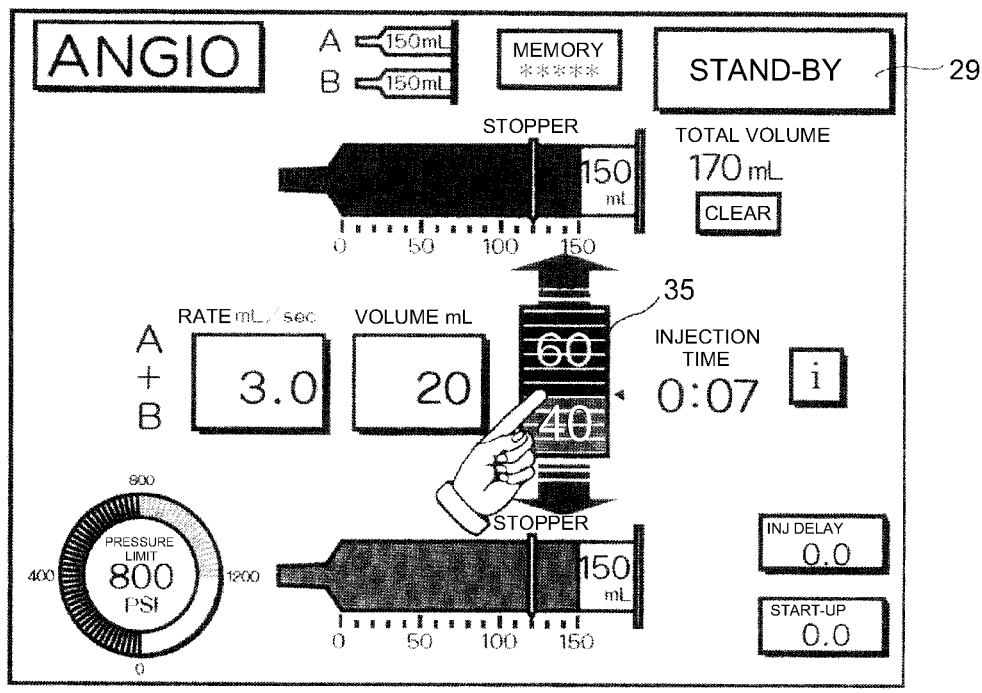
FIG. 5 is a diagram showing how to change a mixture ratio by touching an image button.

Simultaneously with or subsequently to (by way of example) the input of the injection rate and the like, the mixture ratio (50:50 in this case) may be input. The input may be performed through automatic setting of a predetermined mixture ratio (50:50) as a default value. The operator can change the mixture ratio as required. To change the ratio, the operator can touch a part of image 35 with his fingertip as shown in FIG. 5 and move his fingertip up or down to change the mixture ratio. On a screen shown in FIG. 5, the mixture ratio is then changed to "60/40," by way of example.

After the input for the injection rate, the injection volume, and the mixture ratio is completed as described above, the controller unit 50 performs:

a process of calculating the injection rate of the contrast medium (1.5 ml/sec) based on the input mixture ratio;

a process of calculating the injection rate of the physiological saline (1.5 ml/sec) based on the input mixture ratio;

a process of calculating the injection volume of the contrast medium (10 ml) based on the input mixture ratio; and a process of calculating the injection volume of the physiological saline (10 ml) based on the input mixture ratio.

When the mixture ratio is changed, the controller unit 50 performs:

a process of calculating the injection rate (1.8 ml/sec) of the contrast medium based on the changed mixture ratio;

a process of calculating the injection rate (1.2 ml/sec) of the physiological saline based on the changed mixture ratio;

a process of calculating the injection volume (12 ml) of the contrast medium based on the changed mixture ratio; and a process of calculating the injection volume (8 ml/sec) of the physiological saline based on the changed mixture ratio.

Figure 6:
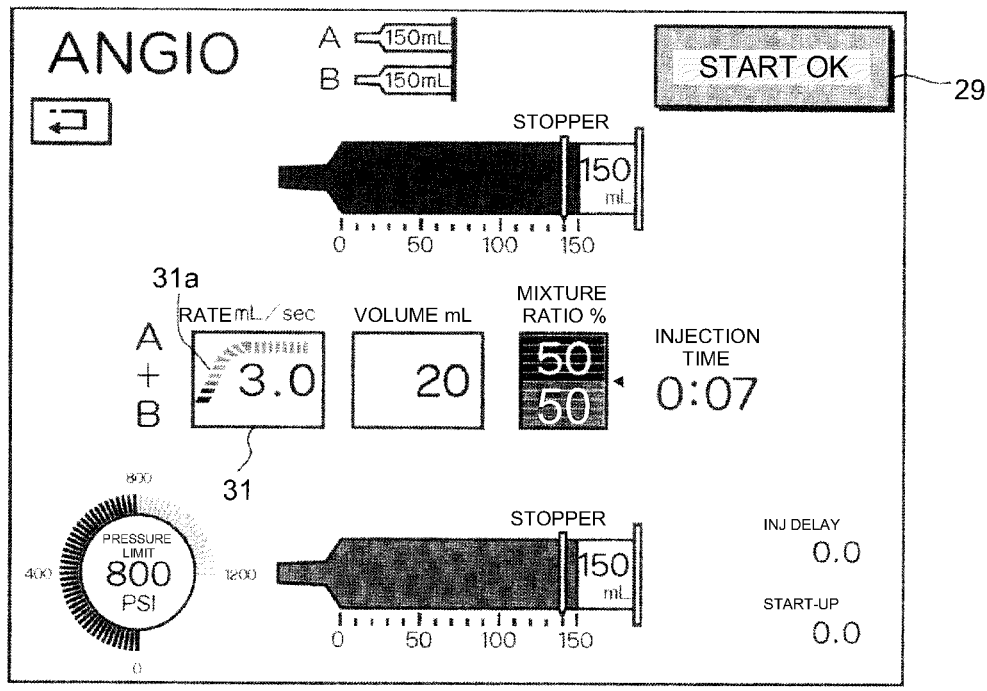
FIG. 6 is a diagram showing images displayed when a stand-by button is pressed on the screen of FIG. 2.

After the setting of the injection conditions is completed through the abovementioned steps, the operator presses a stand-by button 29 (see FIG. 2) at the upper right on the screen. Then a screen as shown in FIG. 6 will appear. FIG. 6 shows an example of the screen in which the mixture ratio is 50:50. On the screen, an indicator 31*a* for visually displaying the injection rate is also displayed in the image 31 showing the injection rate. "START OK" is displayed on button 29 at the upper right on the screen.

Next, the operator presses button 29 of "START OK" or presses a certain button, not shown, on the injector head to start a medical fluid injection. Specifically, each piston driving mechanism of the injector head 110 operates to inject each medical fluid at a predetermined injection rate (for example, 1.5 ml/sec) calculated through the abovementioned steps. In this example, the same volume of the medical fluids are pushed out from syringes A and B simultaneously to inject the patient with the diluted contrast medium provided by mixing the contrast medium and the physiological saline at the ratio of 1:1.

When the injection of 20 ml of diluted contrast medium is completed, the operation of the injector will be automatically finished.

According to the medical fluid injector device of the present embodiment described above, a programming for injection conditions can be completed by inputting three numeric values, that is, the injection rate, the injection volume, and the mixture ratio of the diluted contrast medium. With such a configuration, injection conditions can be set more simply than an input method in which an injection rate and an injection volume need to be set respectively for each medical fluid.

In the present invention, it is conceivable that a system will inject a contrast medium at predetermined mixture at a predetermined injection rate after inputting an injection rate of diluted contrast medium or a mixture ratio of the diluted contrast medium.

The above embodiment has been described with the example in which the contrast medium and the physiological saline are injected, however, the present invention is not limited thereto. For example, two types of contrast medium may be mixed, or an anticancer drug may be diluted with physiological saline.

Although the above embodiment has been described with the example in which the mixture ratio is changed by manipulating the screen (in FIG. 2, for example), such a change may be performed through a voice input. This can be achieved by providing the medical fluid injector device with the unit of receiving voice input. According to the configuration, a doctor can change a mixture ratio without touching apparatus even during medical operation.

Other Embodiment 1

The present invention is not limited to the above embodiment, various modifications may be made. For example, as shown in FIG. 7, the mixture ratio may be changed during the medical operation (step S3a), after injection conditions for diluted contrast medium have been programmed (step S1) similarly to the above embodiment and then the injection (i.e. medical operation) has started (step S2).

In an angiography evaluation, the following procedure may be performed. A catheter is inserted into a predetermined region of interest (ROI) in a patient's body. Then, the diluted contrast medium of a certain concentration will be injected to examine the region. A tip of the catheter will be moved into a different region of interest, and a diluted contrast medium at a different concentration will be injected to examine the region. In such an examination, it is necessary to inject diluted contrast mediums at different concentrations during the medical operation. According to the configuration in which the mixture ratio can be changed during the procedure as in the present embodiment, diluted contrast medium at suitable concentration for each region of interest can be injected.

Figure 7:
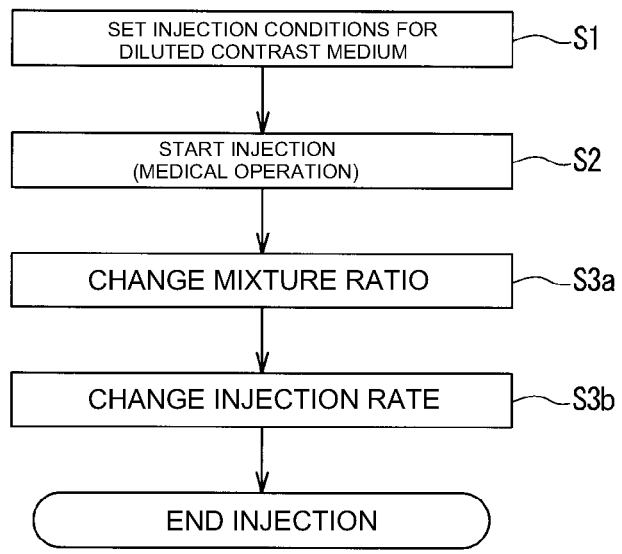
FIG. 7 is a flow chart for describing another example of operation according to the present invention.

As shown in FIG. 7, an injection rate of diluted contrast medium may be changed during medical operation (step S3b). For example, in order to change the injection rate the operator can manipulate the hand controller of controller unit 50. Only the injection rate may be changed, while the mixture ratio is kept constant.

According to the configuration in which the injection rate can be changed during the medical injection, the contrast medium can be injected under conditions suitable for each region of interest similarly to the above case. It should be noted that the device according to the present invention may have only one of the functions described at step S3a and S3b.

As other example, an image button may be displayed on the monitor of controller unit 50, and when the button is pressed, the completion of the injection of the diluted contrast medium may be followed by subsequent injection of a predetermined volume of physiological saline.

According to this configuration, the contrast medium remaining in a tube or a catheter can be pushed by the saline. Specifically, the contrast medium remaining in the tube or the catheter can be injected into the patient at a desired pressure until all contrast medium is used, therefore the favorable visualization effect can be achieved to the end.

As yet another example, it is possible to press an ANGIO button displayed at the upper left on the screen in FIG. 2 to switch between a mode (A mode) in which only the contrast medium in syringe A is injected and a mode (B mode) in which only the physiological saline in syringe B is injected. More specifically, it is possible to press the button to switch A mode, B mode, and A+B mode in which the medical fluids in both syringes A and B are injected sequentially.

If a system does not have a mode for injecting only the medical fluid from one of the syringes, it would be necessary to program the mixture ratio from 50:50 (by way of example) to 100:0 (by way of example) in order to inject a contrast medium without dilution. Furthermore, after the injection, it would be necessary to program 50:50 (by way of example) to perform dilution injection. On the other hand, according to the system in which the modes are changeable described above, such an operation for changing the mixture ratio does not need to be performed, so that favorable usability is provided.

Other Embodiment 2

Figure 8:
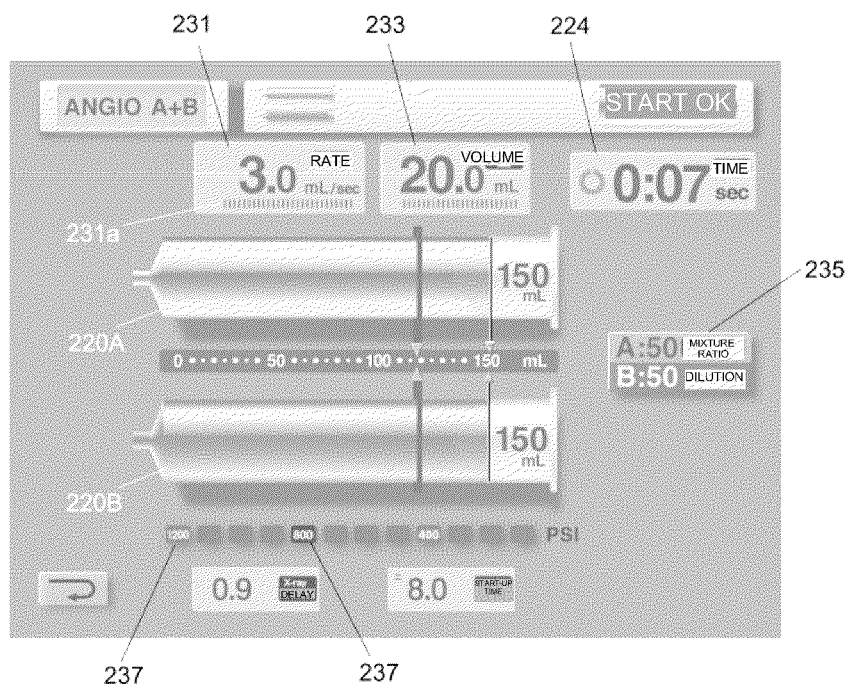
FIG. 8 is a diagram showing an example of other screen displayed on the monitor.
Figure 9:
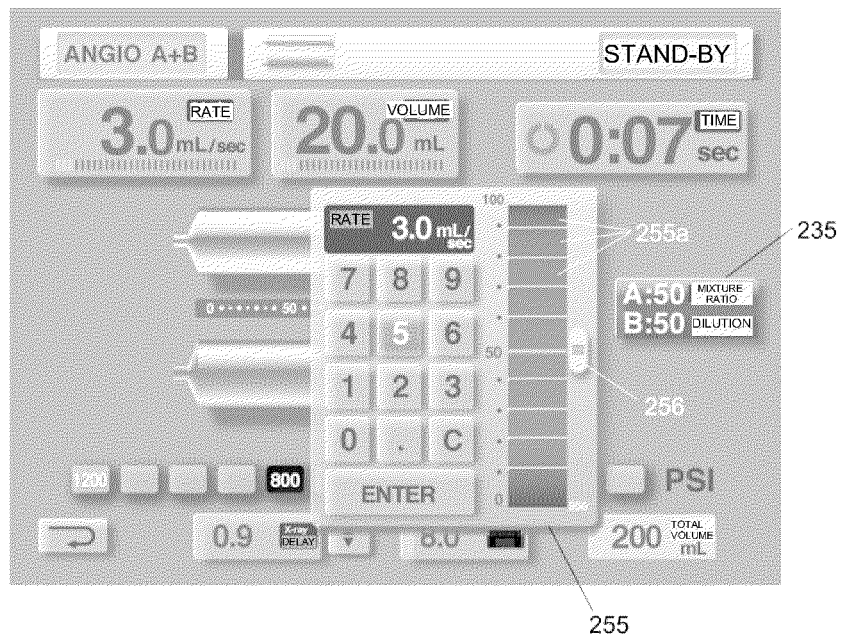
FIG. 9 is a diagram showing an example of another screen displayed on the monitor.

It is conceivable that screens as shown in FIG. 8 and FIG. 9 may be displayed on the medical fluid injector device according to the present invention. In this example, two syringe images 220A and 220B are displayed on the screen, similarly to the above embodiment. A scale, for example from 0 ml to 150 ml, showing a volume of medical fluid in the syringe is displayed between syringe images 220A and 220B.

On the screen, an image 231 corresponding to the image 31 in the above embodiment is displayed. An injection rate of diluted contrast medium is displayed in the image 231, in this example, "3.0" (ml/sec) is displayed. The image 231 also functions as a button. When the image 231 is pressed, a numeric keypad (not shown) appears. The numeric keypad can be manipulated to change the injection rate.

An indicator 231a including a plurality of segments arranged horizontally is displayed in the image 231. The indicator 231a refers to a range of rates within which the system can be programmed. For example, assume that an upper limit of rate is 10 ml/sec, when a rate of 3.0 ml/sec is selected, 30% of all the segments will be displayed in a predetermined color. Such indicators 231a allow the operator to know intuitively a level of a currently set value relative to the upper limit value of rate.

As shown in FIG. 8, an image 233 corresponding to the image 33 in the above embodiment is displayed on the screen. The injection volume of diluted contrast medium is displayed in image 233, in this example, "20" (ml) is displayed. The image 233 also functions as a button similarly to the image 231. When the image 233 is pressed, a numeric keypad similar to the abovementioned one appears. An indicator similar to the indicator 231a described above is also displayed in the image 233.

An image 235 (FIG. 8) shows a mixture ratio of a contrast medium and a physiological saline. To change the mixture ratio, the image 235 is pressed by the operator to display a window 255 as shown in FIG. 9. A plurality of (10 in this example) color segments 255a arranged vertically are displayed in window 255 in addition to a numeric keypad and the like. Each segment 255a functions as a button. For example, if the operator selects the segment 255a at the second from the top, then the mixture ratio will be programmed at 90:10.

A slider 256 capable of sliding vertically on the screen is also displayed in the window 255. The mixture ratio can also be changed by moving the slider 256 vertically.

On the screen shown in FIG. 8, a plurality of image buttons 237 for setting a pressure limit value of medical fluid are displayed below the syringe image 220B, by way of example. The plurality of image buttons 237 are arranged in a line horizontally in this example. Twelve image buttons 237 may be displayed and correspond to 1200, 1100, 1000, 900, 800, 700, 600, 500, 400, 300, 200, and 100 PSI in order from the left. Although not limited particularly, the numerals of the pressure limit values are displayed only on image buttons 237 for 1200, 800, and 400 PSI, and no numerals are displayed on the other buttons.

The operator selects one of the image buttons 237 to set the pressure limit value of medical fluid. As in a known control method, an alarm may be generated when a pressure of medical fluid during medical fluid injection exceeds a predetermined pressure limit, for example. Alternatively, the system may control its operation so that the medical fluid pressure can be reduced.

Other Embodiment 3

Figure 10:
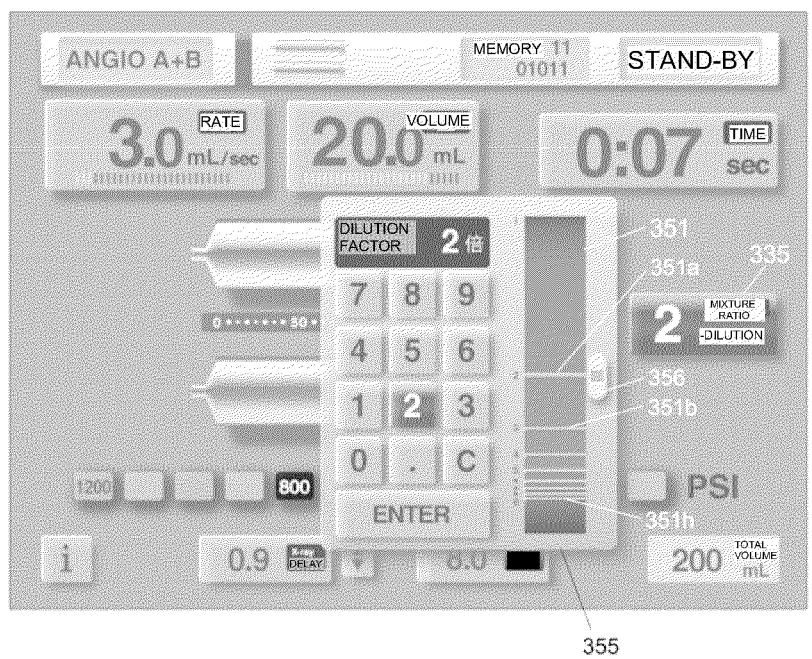
FIG. 10 is a diagram showing an example of condition setting with a mixture factor.

A screen as shown in FIG. 10 may be displayed in the medical fluid injector device of the present invention. In this example, injections conditions can be programmed by using a "mixture factor" instead of the "mixture ratio" as shown in FIG. 2.

A factor display portion 351 extending vertically is displayed in a window 355 as shown in FIG. 10. Numbers from 1 to 9 are displayed on the side of the display portion 351 (Number 6 to 8 are displayed by dots). The numbers represent mixture factors.

For example, the mixture factor "one" means that a contrast medium should be injected without dilution. The mixture factor "two" means that a contrast medium should be diluted by a factor of two (that is, the mixture ratio 50:50). To allow intuitive understanding of this, the number "2" is displayed substantially at the center of vertically extending display portion 351.

The mixture factor "three" means that the contrast medium should be diluted by a factor of three (that is, the mixture ratio 1:2). To allow intuitive understanding of this, the number "3" is displayed at a position which divides the vertically extending display portion at a proportion of 1:2 (2 for the contrast medium). For mixture factors 4 to 9, the numbers are also displayed at positions defined in the same manner.

Horizontal lines 351a to 351h are displayed in association with the respective positions from the numbers 2 to 9. A vertically slidable slider 356 is displayed at the right of vertically extending display portion 351. The operator can touch and move the slider 356 vertically to select a desired mixture factor. The slider may be moved by touch with a finger or by an input pen or the like.

Although not limited particularly, the selected mixture factor is displayed as a character in an image 335. In the example of FIG. 10, "2" is selected with slider 356, and "two-fold dilution" is displayed in the image 335.

According to the configuration as shown in FIG. 10, since mixture conditions can be programmed based on the mixture factor, the doctor can use various setting methods, and a device with more favorable usability can be provided.

It goes without saying that the embodiment in which the mixture factor is input as shown in FIG. 10 can be combined with other embodiments described above as appropriate. For example, the mixture factor may be input through voice input means.

Processes after inputting the mixture factor may be similar to those in the above embodiment. For example, when "three" is input as the mixture factor, an injection rate of contrast medium is calculated based on the mixture factor (by way of example, 1.0 ml/sec), whereas injection rate of physiological saline is calculated based on the mixture factor (by way of example, 2.0 ml/sec).

With respect to a volume of mixed medical fluid being displayed as 20 ml in FIG. 10, for instance, when "three" is input as the mixture factor, the volume of contrast medium may be calculated based on that mixture factor (20×0.333 . . . ml), whereas the injection rate of physiological saline may be calculated based on that mixture factor (20×0.666 . . . ml).

Each medical fluid will be injected based on the injection rate and the injection volume calculated as described above.

It should be noted that a numeric keypad might also be displayed in the window 355 in FIG. 10. The mixture factor can also be set by directly inputting a numeric value through the numeric keypad.

[Input with Iodine Concentration]

Numeric values of the concentration for diluted medical fluid may be important in some situation in which contrast medium diluted with the physiological saline is injected. For example, a doctor sometimes needs specific concentration such as an iodine concentration of 370 mgI/ml to inject diluted contrast medium into a region of interest of the patient.

To achieve this, it is conceivable that a system is configured to display a plurality of options for iodine concentration (for example, 400, 370, 350, 320, 300, 250, and 200 mgI/ml) on its screen. In response to selection of one of them, a specific injection rate of medical fluid will be automatically programmed so as to provide the diluted contrast medium having the selected iodine concentration.

For example, assume that a contrast medium has an iodine concentration of 400 mgI/ml. In this case, when the operator selects 400 mgI/ml of the plurality of options, no dilution is needed and only the contrast medium is injected (that is, the injection at a mixture ratio of 0:100). When the operator selects 200 mgI/ml, for example, the injection rate and the injection volume of each medical fluid will be automatically changed so as to provide a mixture ratio of 50:50. The medical fluid injection will be performed under the reset conditions.

According to the abovementioned configuration, since the injection conditions can be programmed by using the numeric value of the iodine concentration as a parameter, the medical fluid injector device can be provided with more favorable usability.

[Manipulation with Hand Switch]

It is conceivable that the hand controller of the controller unit may be manipulated to perform the following medical fluid injection. For example, during medical fluid injection at a certain mixture ratio (by way of example, 50:50), the hand controller can be used so as to change only the injection rate with the mixture ratio maintained. This allows favorable imaging suitable for each region of interest within the patient's body.

Alternatively, it is possible to manipulate the hand controller during medical fluid injection to change only the mixture ratio with the injection rate maintained.

Although the example of the present invention has been described, the present invention is not limited thereto, for example, input means such as a mouse and a keyboard may be used instead of the touch panel to input the predetermined information to controller unit 50. Controller unit 50 may be connected to a network, and the information such as the injection rate, the injection volume, the mixture ratio and the like of the diluted contrast medium may be input to controller unit 50 through the network.

[Example of Other Screens and Functions]

Figure 11:
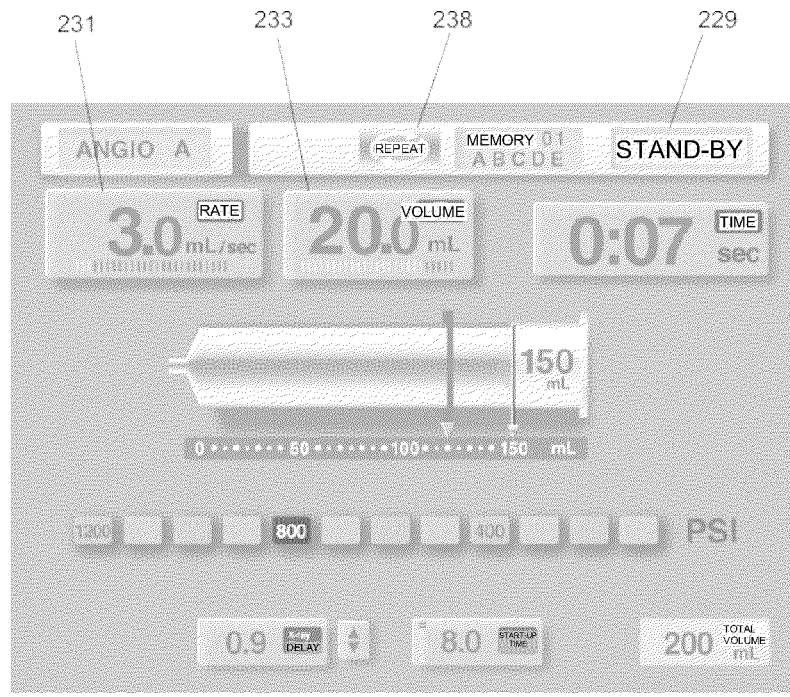
FIG. 11 is a diagram showing an example of another screen displayed on the monitor.

FIG. 11 shows an example of other screen displayed on the monitor. On this screen, a button 238 "repeat" is displayed. Other icons (for example, images 231 and 233) are basically identical to those in FIG. 8, but "stand-by" is displayed on button 229 in FIG. 11.

The repeat button 238 is used for repeatedly performing injections under the same conditions as the previous conditions. By way of example, assume that 20 ml of contrast medium is injected at a rate of 3.0 ml/sec in the previous injection and that a sufficient volume of medical fluid remains in the syringe after that injection. In this case, the repeat button 238 is pressed, and then the stand-by button 229 and a button, not shown, on the injector head are pressed to execute the injection under the same conditions as the previous conditions (at a rate of 3.0 ml/sec and a volume of 20 ml). Such a repeat injection is particularly useful for the procedure such as an angiography evaluation in which a relatively small volume of contrast medium is repeatedly injected. The repeat injection can be performed as long as the volume of medical fluid in the syringe is larger than a predetermined limit (20 ml in this example).

With respect to FIG. 11, it is conceived that a predetermined button "BACK" may be displayed on the screen when the repeat button 238 and the stand-by button 229 are pressed (the image "stand-by" is changed to "start OK"). This button can be pressed to return to the setting screen, and the injection conditions can be changed again on the setting screen.

Figure 12:
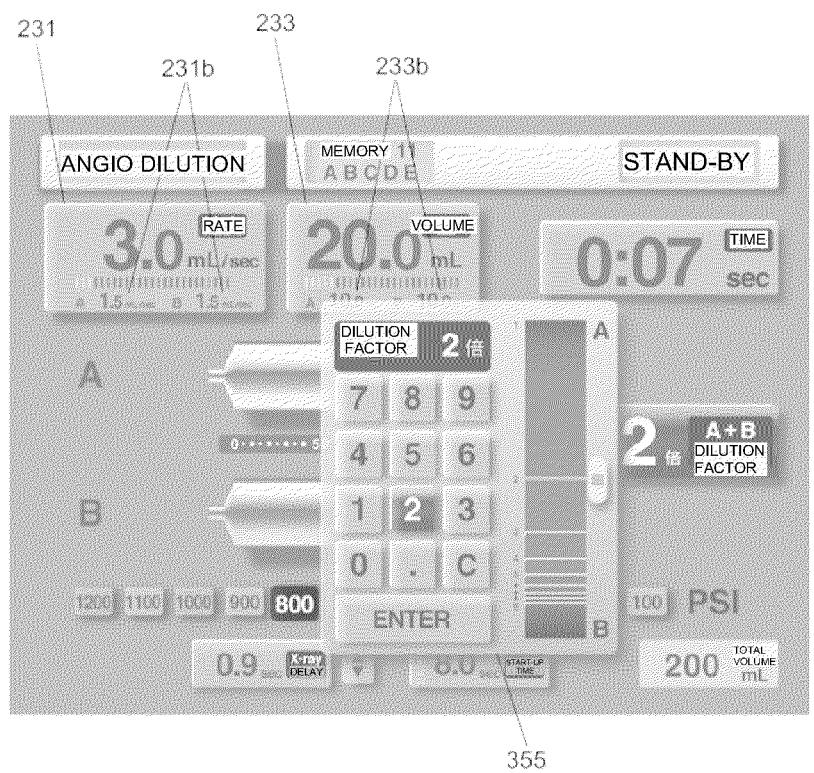
FIG. 12 is a diagram showing an example of yet another screen displayed on the monitor.

FIG. 12 shows an example of yet other screen displayed on the monitor. Although the injection rate and the injection volume are displayed by pressing the information button 25 in the mode shown in FIG. 2 and the like, the present invention is not limited thereto. As shown in FIG. 12, injection rate 231b of the medical fluid (by way of example, A: 1.5 ml/sec, B: 1.5 ml/sec) may be displayed in the image 231, whereas injection volume 233b of the medical fluid (by way of example, A: 10.0 ml, B: 10 ml) may be displayed in the image 233.

In this case, switching may be made between the display mode as shown in FIG. 12 and the mode using information button 25 as shown in FIG. 2.

LIST OF REFERENCE NUMERALS

25 INFORMATION BUTTON
28 INDICATOR IMAGE
31, 32, 33 IMAGE BUTTON
35 IMAGE (MIXTURE RATIO)
41 NUMERIC KEYPAD
50 CONTROLLER UNIT
51 DISPLAY
110 INJECTOR HEAD
231, 233 IMAGE BUTTON
238 REPEAT BUTTON
255 WINDOW
300 IMAGING DIAGNOSTIC APPARATUS
302 APPARATUS BODY
303 BED
355 WINDOW

The invention claimed is:

1. A medical fluid injector device, comprising:
an injector head which injects a mixed medical fluid comprising a first medical fluid and a second medical fluid into a patient; and
a controller unit operably connected to the injector head, wherein the controller unit comprises a monitor on which a graphical user interface for changing an injection condition is displayed, wherein the monitor consists of components for displaying images and responding to touch input,
wherein the controller unit is configured to:
display a current mixture factor of the mixed medical fluid;
display the graphical user interface, comprising a window that includes (i) a mixture factor display portion extending vertically and consisting of a plurality of segment images, (ii) a plurality of mixture factor numerals displayed on a side of the mixture factor display portion, (iii) a slider icon for changing the mixture factor, and a numeric key pad for changing the mixture factor, wherein each mixture factor numeral is displayed at a position that divides the mixture factor display portion into 1:N−1, wherein N is the mixture factor, and wherein the graphical user interface further includes an image which shows the current mixture factor;
receive an input for changing the current mixture ratio or mixture factor by an operator via the graphical user interface; and
recalculate an injection rate of the first medical fluid and the second medical fluid based on a new mixture factor.

2. The medical fluid injector device of claim 1, wherein the plurality of segment images are colored and aligned.

3. The medical fluid injector device of claim 2, wherein each segment image serves as an icon for changing the mixture factor by selecting one of the segment images.

4. The medical fluid injector device of claim 1, wherein the controller unit displays the window when an icon on the monitor is selected.

5. The medical fluid injector device of claim 1, further comprising a first syringe for a first contrast medium.

6. The medical fluid injector device of claim 5, further comprising a second syringe for saline or a second contrast medium.

* * * * *

UNITED STATES PATENT AND TRADEMARK OFFICE
CERTIFICATE OF CORRECTION

PATENT NO. : 9,675,749 B2
APPLICATION NO. : 13/639657
DATED : June 13, 2017
INVENTOR(S) : Shigeru Nemoto Page 1 of 1

It is certified that error appears in the above-identified patent and that said Letters Patent is hereby corrected as shown below:

In the Claims

Column 12, Line 35 (Claim 1), after "current" delete "mixture ratio or".

Signed and Sealed this
Twenty-seventh Day of March, 2018

Andrei Iancu
*Director of the United States Patent and Trademark Office*